United States Patent [19]

Steigerwald

[11] Patent Number: 5,009,391
[45] Date of Patent: Apr. 23, 1991

[54] VALVE ASSEMBLY

[75] Inventor: Carl J. Steigerwald, Fox Lake, Ill.

[73] Assignee: The Kendall Company, Mansfield, Mass.

[21] Appl. No.: 611,804

[22] Filed: Oct. 31, 1990

Related U.S. Application Data

[60] Continuation of Ser. No. 453,522, Dec. 20, 1989, abandoned, which is a division of Ser. No. 189,097, May 2, 1988, Pat. No. 4,895,346.

[51] Int. Cl.⁵ .............................................. F16L 37/28
[52] U.S. Cl. ................................. 251/149.1; 137/849; 604/167; 604/247
[58] Field of Search ...................... 137/849; 251/149.1; 604/167, 237, 247, 248, 256

[56] References Cited

U.S. PATENT DOCUMENTS

| | | | |
|---|---|---|---|
| 4,000,739 | 1/1977 | Stevens | 604/167 |
| 4,430,081 | 2/1984 | Timmermans | 604/167 |
| 4,493,475 | 1/1985 | Baird | 251/149.1 |
| 4,610,665 | 9/1986 | Matsumoto | 604/167 |
| 4,673,393 | 6/1987 | Suzuki et al. | 604/167 |
| 4,809,679 | 3/1989 | Shimonaka | 604/167 |
| 4,857,062 | 8/1989 | Russell | 251/149.1 |

FOREIGN PATENT DOCUMENTS 3042229  5/1982  Fed. Rep. of Germany ...... 604/167

Primary Examiner—A. Michael Chambers
Attorney, Agent, or Firm—Alvin Isaacs

[57] ABSTRACT

A valve assembly comprising, a hollow body member having a cavity, a compression member received on one end of the body member and having an annular flange aligned with the cavity, a device for adjusting the position of the compression member relative to the body member, and a valve device for sealingly engaging against a catheter passing through the valve device, and responsive to compression by the compression member to immobilize the catheter in the valve device.

24 Claims, 4 Drawing Sheets

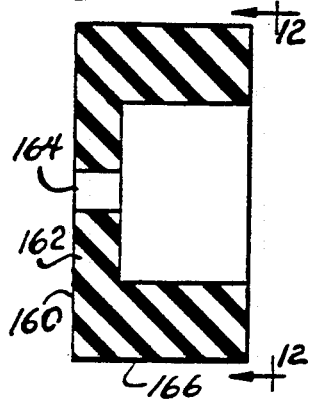
FIG. 11
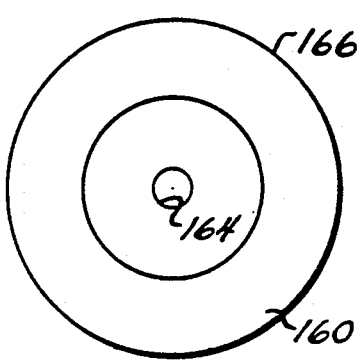
FIG. 12
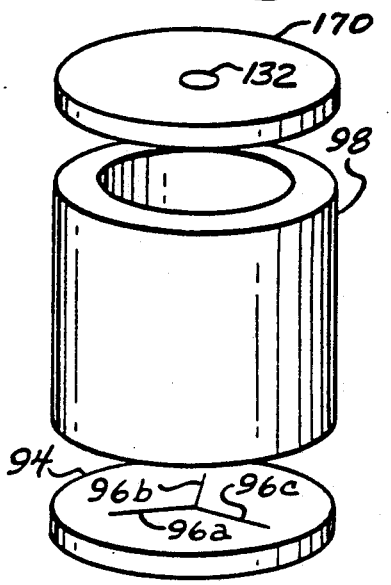
FIG. 13
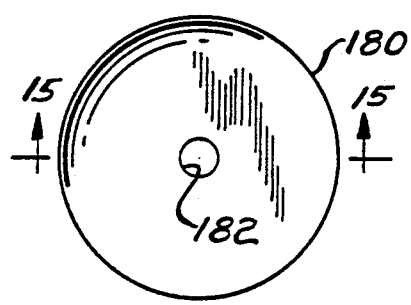
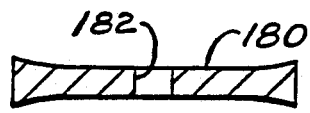
FIG. 14
FIG. 15
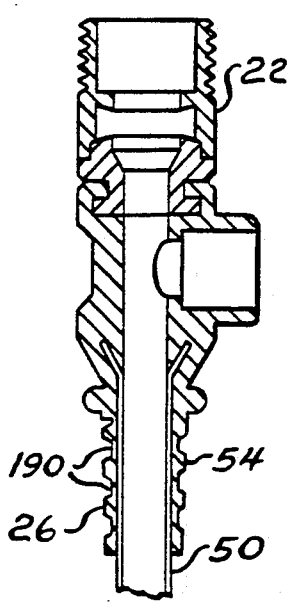
FIG. 16
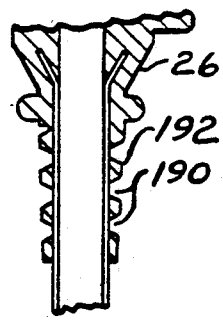
FIG. 17
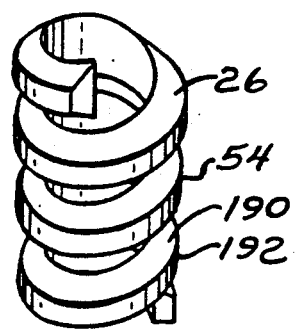
FIG. 18

VALVE ASSEMBLY

This application is a continuation of Ser. No. 453,522 filed Dec. 20, 1989, now abandoned, which in turn is a division of Ser. No. 189,097 filed May 2, 1988 and now U.S. Pat. No. 4,895,346 issued Jan. 23, 1990.

BACKGROUND OF THE INVENTION

The present invention relates to valve assemblies.

In the past, a number of hemostasis valves have been proposed, such as valves disclosed in U.S. Pat. Nos. 4,465,477, 4,626,245, 4,610,665, 4,430,081, 4,354,490, 4,475,548, 4,424,833, 4,240,411, 4,177,814, 3,853,127, 4,705,511, 4,000,739, and 4,436,519. In general, these valve assemblies are designed to seal against a catheter passing through the valves. However, it is desired to improve the operation of the valves, and to immobilize the catheter passing through the valves.

SUMMARY OF THE INVENTION

A principal feature of the present invention is the provision of an improved valve assembly.

The valve assembly of the present invention comprises, a hollow body member having a cavity, a compression member received on one end of the body member and having an annular flange aligned with the cavity, and means for adjusting the position of the compression member relative to the body member. The valve assembly has at least one valve member received in the cavity.

A feature of the invention is that in one form the valve member comprises a pair of discs having slits to receive the catheter.

Another feature of the invention is that the valve member includes an elastic cylindrical sleeve which may be positioned in the cavity intermediate the discs.

Yet another feature of the invention is that the valve member comprises a pair of valve structures having a disc and an intergral annular rim which are positioned in various configurations in the cavity.

A feature of the invention is that the discs and sleeve are maintained in a spaced relationship by a plurality of annular washers.

Another feature of the invention is that the washers have an outwardly directed taper in conjunction with outer wedges formed on the discs to securely hold the discs in place in the valve assembly.

A feature of the invention is the provision of a method for making the valve assembly of the present invention.

Further features will become more fully apparent in the following description of the embodiments of this invention and from the appended claims.

DESCRIPTION OF THE DRAWINGS

In the drawings:

FIG. 11 is a sectional view of another embodiment of a valve element for the valve assembly of FIG. 1;

FIG. 12 is an end view of the valve element taken along the line 12—12 of FIG. 11;

FIG. 13 is an exploded perspective view of a valve structure for the valve assembly of FIG. 5;

FIG. 14 is a plan view of another embodiment of a disc for the valve assemblies of FIGS. 7-9;

FIG. 15 is a sectional view taken substantially as indicated along the line 15—15 of FIG. 14, showing wedges formed on the disc;

FIG. 16 is a sectional view showing another embodiment of a transition member for the valve assembly of the present invention;

FIG. 17 is a sectional view showing another embodiment of a transition member for the valve assembly of the present invention; and FIG. 18 is a fragmentary perspective view of a distal end portion of the transition member of FIG. 17.

DESCRIPTION OF THE PREFERRED EMBODIMENTS

Figure 1:
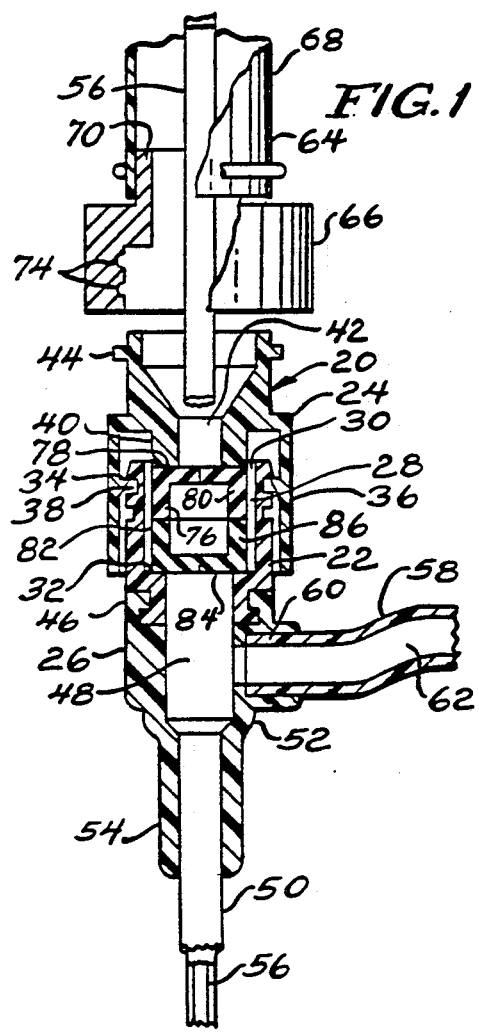
FIG. 1 is a fragmentary sectional view of a valve assembly of the present invention.
Figure 2:
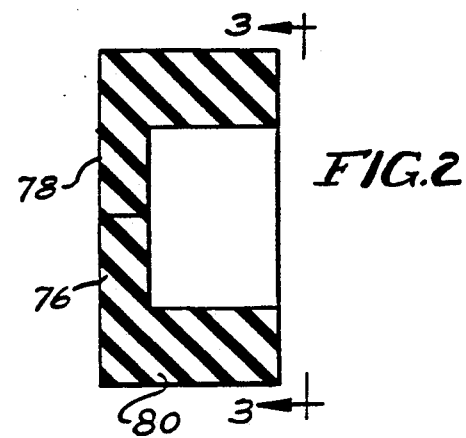
FIG. 2 is a sectional view of a valve member for the valve assembly of FIG. 1.
Figure 3:
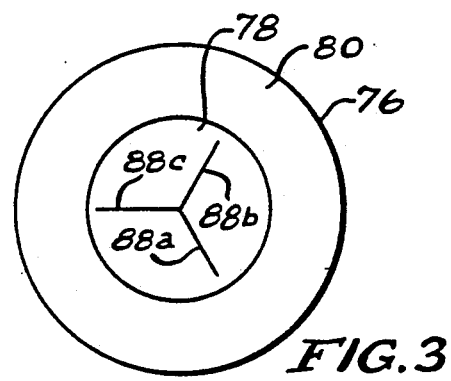
FIG. 3 is an end view of the valve member of FIG. 2 taken along the line 3—3.

Referring now to FIGS. 1-3, there is shown a valve assembly generally designated 20 having a hollow body member 22, a compression member 24, and a hollow transition member 26.

As shown, the body member 22 has an internal cavity 28 defining an opening 30 adjacent a proximal end of the body member 22, and an annular shoulder 32 adjacent a distal end of the body member 22. The body member 22 has an external threads 34 on an outer surface thereof adjacent the proximal end of the body member 22.

The compression member 24 has an annular rim 36 extending over the outer surface of the body member 22, and having internal threads 38 cooperating with the threads 34 of the body member 22 in order to adjust the compression member 24 relative to the body member 22. The compression member 24 has an internal annular flange 40 aligned with the cavity 28 of the body member 22 for a purpose which will be described below, with the flange 40 defining a port 42. The proximal end of the compression member 24 has external threads 44 for a purpose which will be described below.

The transition member 26 has a proximal end 46 fixedly secured to a distal end of the body member 22, and a channel 48 extending therethrough. As shown, the valve assembly 20 has an elongated sheath 50, such as urethane, with a proximal tapered portion 52, with the sheath 50 being fixedly secured in a distal end of the transition member 26. The transition member 26 has an an outer distal tapered portion 54 surrounding the proximal portion of the sheath 50 to provide strain relief for the sheath 50 and reduce the possibility of kinking of the sheath when there is no catheter 56 extending through the sheath 50 during bending of the sheath 50. The valve assembly 20 has an elongated conduit 58 of enlarged diameter secured to a side port 60 of the transition member 26, with a lumen 62 of the conduit 58 being in fluid communication with the channel 48 of the transition member 26 for a purpose which will be described below.

The valve assembly 20 has a covering member 64 for the catheter 56 having a connection member 66 and an elongated flexible sleeve 68 attached to an annular flange 70 of the connection member 66 by an 0-ring 72. The connection member 66 has internal threads 74 which cooperate with the threads 44 of the compression member 24 in order to releaseably lock the connection member 66 onto the proximal end of the compression member 24.

The valve assembly 20 has a first elastic valve member 76 received in the cavity 28 of the body member 22, with the first valve member 76 having a circular disc 78, and an integral annular rim 80 extending from the disc 78. The valve assembly 20 has a second valve member 82 also received in the cavity 28 of the body member 22, with the second valve member 82 having a disc 84, and an integral annular rim 86 extending from the disc 84.

The first valve member 76 is illustrated in FIGS. 2 and 3, and, as shown, the disc 78 has three slits 88a, 88b, and 88c extending from a juncture of the slits 88a, b, and c for a purpose which will be described below. The second valve member 82 also has three slits in an identical configuration with that illustrated in connection with the first valve member 76.

Figure 4A:
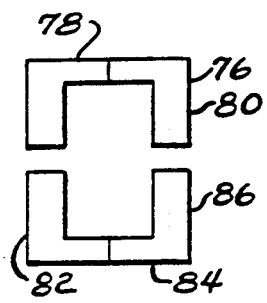
FIGS. 4a, b, c, and d are sectional views of various configurations of valve elements located in the valve assembly of FIG. 1.
Figure 4B:
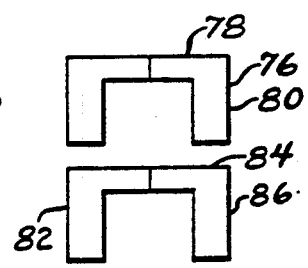
Figure 4C:
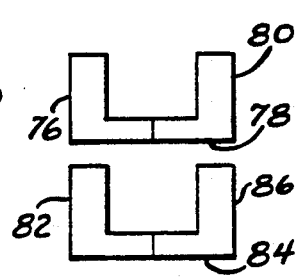
Figure 4D:
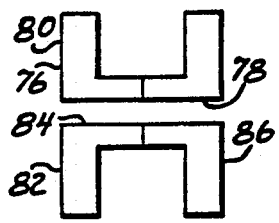

As shown in FIG. 4a, the first and second valve members 76 and 82 may be arranged in the cavity 28 with the rim 80 of the first valve member 76 being in contact with the rim 86 of the second valve member 82. As shown in FIG. 4b, the first and second valve members 76 and 82 may be arranged in the cavity 28 with the rim 80 of the first valve member 76 being in contact with the disc 84 the second valve member 82. As shown in FIG. 4c, the first and second valve members 76 and 82 may be arranged in the cavity 28 with the disc 78 of the first valve member 76 being in contact with the rim 86 of the second valve member 82. As shown in FIG. 4d, the first and second valve members 76 and 82 may be arranged in the cavity 28 with the disc 78 of the first valve member 76 being in contact with the disc 84 the second valve member 82. The first and second valve members 76 and 82 may be constructed from a suitable elastic material, such as silicone, natural rubber, or thermoplastic elastomer.

In use of the assembly 20, first, an intravenous catheter and needle assembly, with the needle located inside the catheter, is inserted into a suitable vein, such as the jugular or subclavian vein in the region of the neck, and once inserted into the vein, the needle is removed from the catheter. Next, a guide wire is inserted through the catheter until it is located in the vein, and the catheter is removed over the guide wire. Next an enlarged dilator having a channel extending therethrough is passed into the sheath 50 through the valve assembly 20, and the dilator is passed over the guide wire until the sheath 50 is located in the vein. At this time, the dilator and guide wire are removed from the valve assembly 20, with the sheath in place in the vein. At this time, the conduit 58 and sheath 50 may be flushed, or the conduit 58 and sheath 50 may be flushed before placing the sheath 50 in the vein. The catheter 56 may be passed through the valve assembly 20 and sheath 50 either before or after attachment of the covering member 64 to the compression member 24. In any event, once the covering member 64 is locked in place, and the catheter 56 is inserted through the valve assembly 20, the flexible sleeve 68 is extended over the catheter 56, with the sleeve 68 protecting the catheter 56 during use of the device.

The inserted catheter 56 extends through the compression member 24, the port 42, the slits of the first and second valve member 76 and 82, and through the sheath 50 into the vein. The catheter 56 may be utilized to infuse drugs into the venous system during use of the device. In the assembled configuration, there is a slight clearance between the catheter 56 and the sheath 50, and the conduit 58 is made relatively large to infuse drugs through the conduit 58, and past the catheter 56 through the sheath 50 into the vein in order to feed a solution, such as heparin, into the vein to prevent clotting. As previously indicated, the tapered portion 54 of the transition member 26 prevents kinking of the catheter 56 during use, and the connection member 66 of the covering member 64 prevents the sleeve 68 from being inadvertently removed from the compression member 24.

As previously discussed, the catheter 56 passes through the first and second valve members 76 and 82, and the valve members 76 and 82 seal against the catheter 56 in order to prevent passage of air into the sheath 50, and prevent the passage of blood out through the valve members 76 and 82. Two valve members i.e., the first and second valve members 76 and 82, are utilized in the event that one of the valve members is damaged, then the other valve member is used as a back up precaution for the other valve member. With the catheter 56 in place in the valve assembly 20, the compression member 24 may be adjusted relative to the body member 22 in order to apply pressure by the annular flange 40 against the first and second valve members 76 and 82 to bulge the rim 80 of the first valve member 76 and the rim 86 of the second valve member 82 against the catheter 56 in order to immobilize and hold the catheter 56 in place in the valve assembly 20. In the event that the catheter 56 is removed from the valve assembly 20, further compression may be applied by the compression member 24 against the first and second valves 76 and 82 in order to further bulge the rims 80 and 86 inwardly and close the cavity 28 of the body member 22 in order to insure that no air or blood passes through the first and second valve members 76 and 82. The closed slits of the first and second valve members 76 and 82 further assure that no air or blood will pass through the first and second valve members 76 and 82 when the catheter 56 is removed from the valve assembly 20.

In accordance with a method of manufacture of the valve assembly 20, first the body member 22 is formed from a rigid material, such as urethane, and the body member 22 and preformed sheath 50, such as urethane, are placed in a spaced relationship in a mold. Next, the transition member 26 is injected molded from a suitable material, such as urethane, in order to form an intergral sealed construction of the sheath 50 and the body member 22, such that the body member 22, transition member 26, and sheath 50 are intergrally formed into one piece in a manner preventing leakage of air or blood from the bonds of the various pieces.

Figure 5:
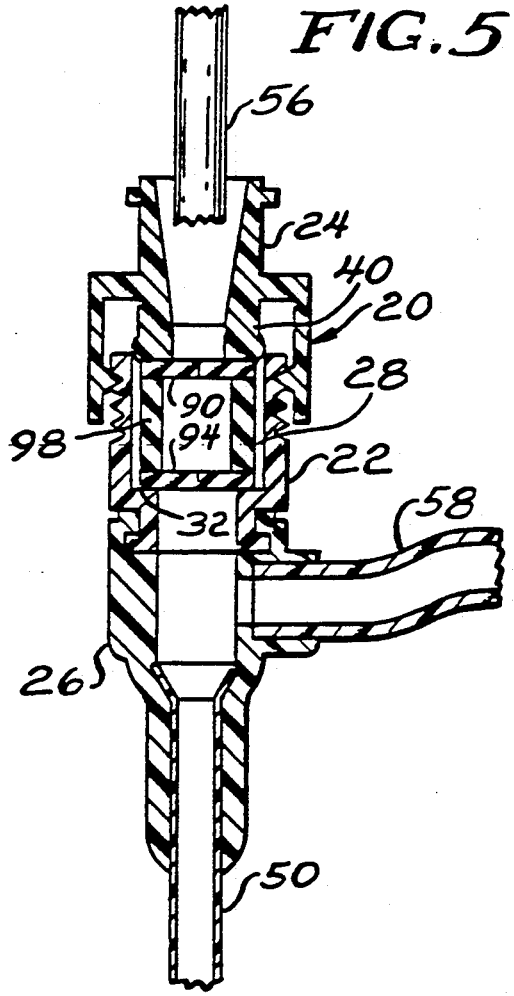
FIG. 5 is a fragmentary sectional view of another embodiment of a valve assembly according to the present invention.
Figure 6:
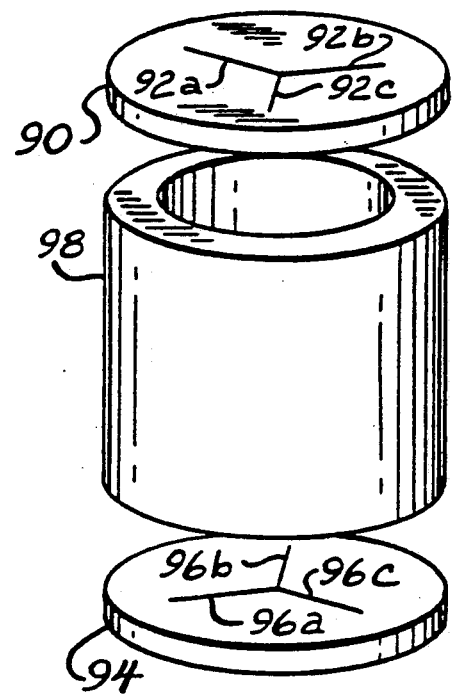
FIG. 6 is an exploded perspective view of a valve structure for the valve assembly of FIG. 5.

Another embodiment of the present invention is illustrated in FIG. 5, in which like reference numerals designate like parts. In this embodiment, the body member 22, compression member 24, transition member 26, and sheath 50 are substantially the same as discussed in connection with FIG. 1. However, in this embodiment, the valve received in the cavity 28 of the body member 22 is in a modified form, as will be discussed below. As shown in FIGS. 5 and 6, the valve has a first elastic disc 90 facing toward the annular flange 40 of the compression member 24, with the first disc 90 preferably having three slits 92a, 92b, and 92c extending from a juncture of the slits. The valve has a second disc 94 which is positioned in a distal part of the cavity 28 on the shoulder 32 of the body member 22, with the second elastic disc 94 having three slits 96a, 96b, and 96c extending through the second disc 94 from a juncture of the slits. The valve has a cylindrical elastic sleeve 98 located intermediate and in contact with the first and second discs 90 and 94.

In use of the device of FIGS. 5 and 6, the catheter 56 is passed through the slits of the first and second discs 90 and 94, with the discs 90 and 94 sealing against an outer surface of the catheter 56. Again, two discs are utilized in the event that one of the disc is damaged, and the other disc serves as a backup precaution for sealing against the catheter in this event. With the catheter 56 in place in the valve assembly 20, the catheter 56 passes through the central bore of the sleeve 98, and when compression is applied by the annular flange 40 of the compression member 24, the sleeve 98 bulges inwardly to immobilize and hold the catheter 56 in place in the sleeve 98. In the event the catheter 56 is removed from the valve assembly 20, further compression by the compression member 24 causes further inward bulging of the sleeve 98 to close off the cavity 28 of the body member 22 and insure additional sealing in addition to the closed slits of the first and second discs 92 and 94 to present passage of air or blood through the valve in the cavity 28.

Figure 7:
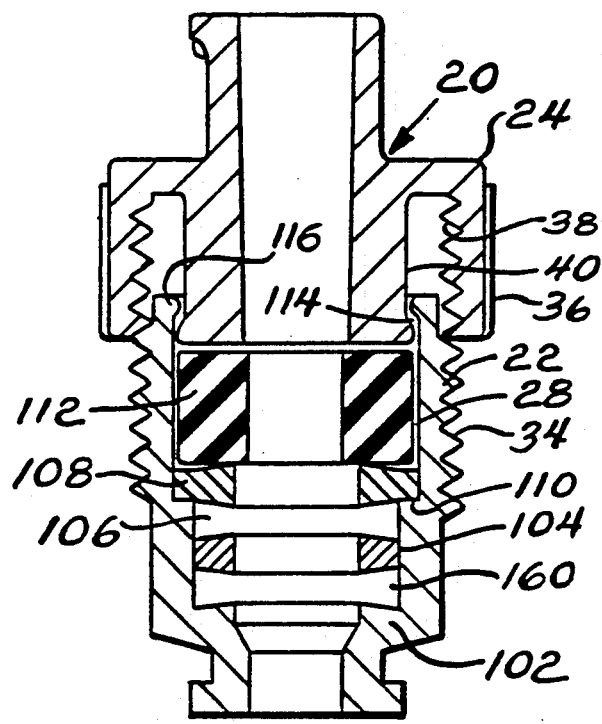
FIG. 7 is a sectional view of another embodiment of a valve assembly of the present invention.

Another embodiment of the present invention is illustrated in FIG. 7, in which like reference numerals designate like parts. In this embodiment, the valve assembly 20 has a first elastic disc 100 adjacent a distal end of the cavity 28 of the body member 22 which rests on an annular shoulder 102 of the body member 22, with the shoulder 102 having an outward taper. An annular tapered first washer 104 is located against and proximal the first disc 100. A second elastic disc 106 is located against and proximal the first washer 104. First and second discs 100, 106 have an outer wedge received in the tape of washer 104, shoulder 102 has an outward taper, and first disc 100 has an outer wedge received in the taper of washer 104, shoulder 102 has an outward taper, and first disc 100 has an outer wedge received in the tapered portion of shoulder 102. A second tapered annular washer 108 is located against and proximal the second disc 106, with the second washer 108 being bonded to an annular shoulder 110 of the body member 22 in order to retain the discs 100 and 106 in place in the unlikely event that the compression member 24 might be inadvertently removed during use of the device, and the discs 100 and 106 will still function to seal the catheter in this event.

The valve assembly 20 has an elastic cylindrical sleeve 112 located proximal the second washer 108 and facing the annular flange 40 of the compression member 24. In a preferred form, the first and second discs 100 and 106 have three slits as previously described, in order to seal against the catheter as it passes through the discs 100 and 106. As shown, the discs preferably have a wedge shape adjacent their outer edges formed by pressure of the washers against the discs, or which may be preformed in order to firmly retain the discs 100 and 106 in place in the washers 104 and 108 as the catheter is passed through the discs 100 and 106. As previously discussed in connection with FIG. 1, the rim 36 has internal threads 38 which cooperate with external threads 34 on the body member 22 in order to adjust the compression member 24 relative to the body member 22. As previously discussed, as the compression member 24 bears against the sleeve 112 with the catheter in place in the valve assembly 20, the sleeve 112 bulges inwardly and immobilizes and retains the catheter in place in the valve assembly 20. If the catheter is removed from the valve assembly 20, further compression by the compression member 24 against the sleeve 112 may occlude the cavity 28 of the body member 22 in order to further assure the prevention of passage of air or blood through the cavity 28 of the body member 22.

As shown, the annular flange 40 has an enlarged distal detent 114 which cooperates with an enlarged proximal detent 116 of the body member 22 in order to minimize the possiblity that the compression member 24 may be removed from the body member 22 when the compression member 24 is unthreaded from the body member 22 to prevent loss of the compression member 24 during packaging or use of the valve assembly 20. Also, the detents 114 and 116 prevent exposure of the sleeve in the cavity 28 of the body member 22 which might otherwise cause the valve to become unsterilized during use.

Figure 8:
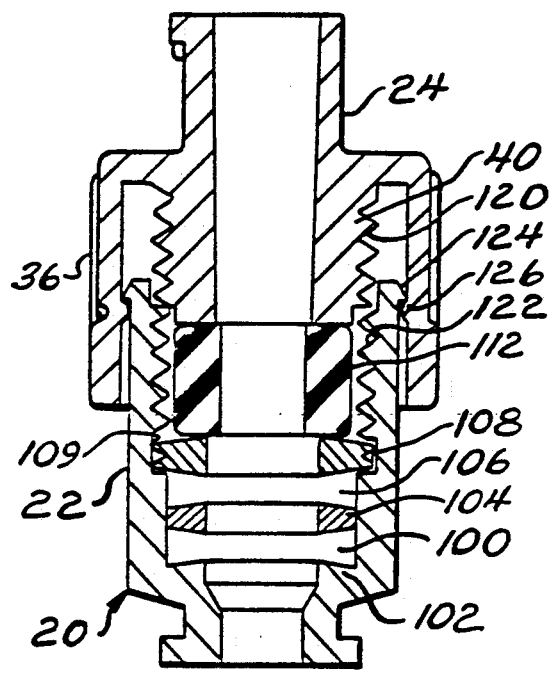
FIG. 8 is a sectional view of another embodiment of a valve assembly of the present invention.

Another embodiment of the present invention is illustrated in FIG. 8, in which like reference numerals designate like parts. In this embodiment, the valve assembly 20 has a first elastic disc 100 with an outer formed or preformed wedge, as previously described, which rests against a tapered distal shoulder 102 of the body member 26 and against shoulder 106 (on body member 20 above disc 106), a first tapered washer 104, a second elastic disc 106 with an outer formed or preformed wedge, as previously described, a second tapered washer 108, and an elastic cylindrical sleeve 112, as previously described in connection with FIG. 7. However, in this embodiment, the second washer 108 has outer threads 109 and is threaded to engage the internal threads of the body member 22 in order to retain the discs 100 and 106 in place in the event that the compression member 24 may be inadvertently removed from the body member 22. The discs 100 and 106 have slits, as previously described, in order to seal against the catheter, and in the embodiments of FIGS. 7 and 8, the discs may be constructed from a suitable elastic material, such as silicone or natural rubber.

In this embodiment, the annular flange 40 of the compression member 24 has external threads 120 which cooperate with internal threads 122 of the body member 22 in order to adjust the compression member 24 relative to the body member 22. Also, the body member 22 has a proximal enlarged external detent 124 which cooperates with an enlarged internal detent 126 of the rim 36 of the compression member 24 in order to minimize the possiblity of removal of the compression member 24 from the body member 22 during packaging or use of the valve assembly 20. In other respects, the valve assembly 20 of FIG. 8 operates in a manner as previously described in connection with FIGS. 1 and 7.

Figure 9:
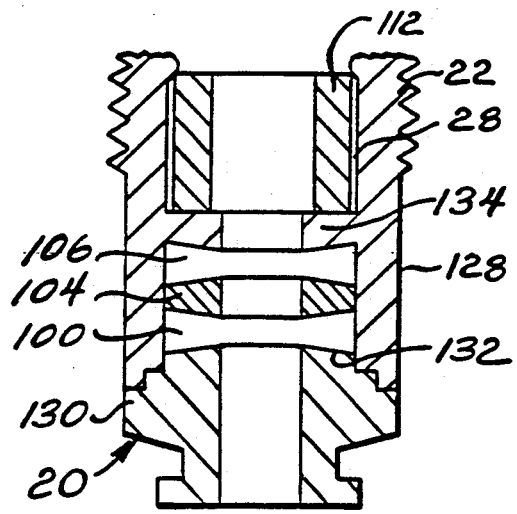
FIG. 9 is a sectional view of another embodiment of a valve assembly of the present invention.

Another embodiment of the present invention is illustrated in FIG. 9, in which like reference numerals designate like parts. In this embodiment, the body member 22 has a separate proximal portion 128 and a distal portion 130 which are joined together i a manner forming an annular groove or shoulder 132 to receive the first elastic disc 100. Body member 22 has annular shoulder 132 adjacent the distal portion of cavity 28, the first disc 100 is received by, and engaged against shoulder 132. As shown, the groove 132 is tapered outwardly to receive the outer formed or preformed wedge portion of the first disc 100. The valve assembly 20 of FIG. 9 also has a tapered first washer 104 which is located against and proximal the first disc 100, and a second elastic disc 106 with an outer formed or preformed wedge placed proximal and against the first washer 104. The proximal portion 128 of the body member 22 has an annular flange or shoulder 134 which engages against the second disc 106 in order to retain it in place, with the flange or shoulder 134 being outwardly tapered to receive the outer formed or preformed wedge of the second disc 106. Body member 22 has annular shoulder 134 intermediate second disc 106 and sleeve 112. The valve assembly 20 of FIG. 9 also has an elastic compression sleeve 112 resting against the annular flange or shoulder 134 which operates in a manner as previously described, with the first and second discs 100 and 106 also having slits and operating in a manner as previously described. The annular flange or shoulder 134 serves to retain the first and second discs 100 and 106 in an operative position in the event that the compression member in this embodiment is removed from the body member 22. Shoulder 134 has an outward taper adjacent second disc 106, and second disc 106 has an outer wedge received in that taper.

Figure 10:
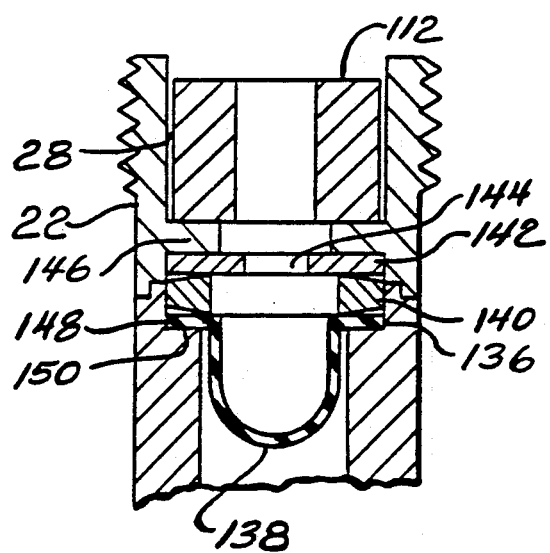
FIG. 10 is a sectional view of another embodiment of a valve assembly of the present invention.

Another embodiment of the present invention is illustrated in FIG. 10, in which like reference numerals designate like parts. In this embodiment, the body member 22 has a distal duckbill valve 136 with a slit 138 to permit passage of the catheter therethrough and seal against the outer surface of the catheter. The valve 136 has an outer annular flange 148 resting on a distal annular shoulder 150 of the body member 22. The body member 22 has a washer 140 located proximal and against the valve 136, and an elastic disc 142 with a central opening 144 located against and proximal the washer 140, with the disc 142 receiving the catheter through the opening 144 of the disc 142 and sealing against the outer surface of the catheter. The body member 22 has an annular flange 146 in order to retain the valve 136, washer 140, and disc 142 in place in event that the compression member is removed from the body member 22. In a preferred form, as shown, the body member 22 has separate proximal and distal portions to facilitate assembly of the device, with the separate portions being connected after assembly. The body member 22 has an elastic cylindrical sleeve 112 which operates in conjunction with the compression member in a manner as previously described. In use, the catheter passes through the sleeve 112, opening 144 of the disc 142, and the slit 138 of the valve 136, with the valve 136 and disc 142 sealing against the outer surface of the catheter. In the event the catheter is removed from the body member 22, the valve 136 prevents passage of air or blood therethrough, and the compression member may be compressed to bulge the sleeve 112 inwardly in order to further close the cavity 28 and prevent passage of air and blood therethrough.

Another embodiment of a third valve member 160 for the valve assembly of FIG. 1 is illustrated in FIGS. 11 and 12. The valve member 160 has a disc 162 with a central opening 164 extending therethrough, and an integral annular rim 166 extending from the disc 162. The valve member 160 may be made from the elastic materials previously described. When the catheter is passed through the opening 164 the portion of the disc 162 surrounding the opening 164 seals against the catheter. The valve member may replace either the first or second valve members 76 or 82 of FIG. 1, and is utilized in conjunction with the other valve member previously described as having a plurality of slits. The third valve member 160 may be located either proximal or distal the other valve member having slit means in the body member cavity 28, and the third valve member may be arranged relative to the other valve member in any of the configurations shown in FIGS. 4a, b, c, and d.

Another embodiment of a valve structure for the valve assembly of FIG. 5 is illustrated in FIG. 13, in which like reference numerals designate like parts. In this embodiment, the valve structure has a third disc 170 having a control opening 172 extending therethrough, with the portion of the disc 120 adjacent the opening 172 sealing against the catheter when it is passed through the opening 172. The third disc may be utilized in conjunction with either the second disc 94, as shown, or the identical first disc 90 having the plural slits. Either the third disc 170 may be located proximal or distal the other disc having slits in the body member cavity 28, and the two discs are utilized in conjunction with the sleeve 98 located intermediate the two discs.

A third disc 180 for the valve assemblies of FIGS. 7-9 is illustrated in FIGS. 14 and 15. The third disc 180 has a central opening 182 extending therethrough, and the third disc 180 seals against the catheter around the opening 182 when the catheter is passed through the opening 182. The third disc 180 may replace either the first or second disc 100 or 106 in the respective valve assemblies of FIGS. 7-9, such that the third disc 180 is utilized in conjunction with a disc having the described slit means and the cylindrical sleeve 112. The third disc 180 may be located either proximal or distal the other disc having slit means in the body member cavity 28, and may be constructed from the previously described elastic materials.

Another embodiment of the transition member 26 for the various previously described valve assemblies is illustrated in FIG. 16, in which like reference numerals designate like parts. In this embodiment, the transition member 26 has a distal tapered end portion 54 surrounding the sheath 50, as previously described. However, in this embodiment, the end portion 54 has an outer sprial groove 190 spaced from the sheath 50 and extending along the end portion 54. In the embodiment of FIGS. 17 and 18, in which like reference numerals designate like parts, the spiral groove 190 extends completely to the sheath 50 in order to define a helical portion 192 of the end portion 54. In this manner, the stiffness of the end portion 54 may be controlled by the depth of the groove 190 in order to permit selective bending of the end portion 54 and prevent kinking of the catheter and sheath 50.

The foregoing detailed description is given for clearness of understanding only, and no unnecessary limitations should be understood therefrom, as modifications will be obvious to those skilled in the art.

What is claimed is:

1. A valve assembly for receiving an elongated element such as a catheter, comprising:
   a hollow body member having a cavity;

a compression member received on one end of the body member and having an annular flange aligned with the cavity;

an elastic duckbill valve having a slit adjacent the distal end of the cavity;

an elastic disc received in the cavity and having a central opening intermediate the valve and the annular flange;

a cylindrical elastic sleeve received in the cavity and having a bore circumferentially surrounded by inner and outer surfaces of the sleeve, the sleeve thickness dimension between the inner and outer surfaces of the sleeve being less than the length dimension of the sleeve;

said slit, opening and sleeve bore being adapted to receive said elongated element and to seal against the outer surface of said element; and means for adjusting the compression member relative to the body member into a plurality of axially spaced apart positions for exerting different axial forces on the sleeve for inwardly bulging the sleeve, so that the sleeve permits passage of the elongated element axially through the bore of the sleeve in a sleeve open position, immobilizes and holds the element in the bore of the sleeve in a sleeve gripping position, and after removal of the element from the bore of the sleeve, inhibits flow of fluid, such as air or blood, through the bore of the sleeve in a sleeve bulged inwardly position.

2. The assembly of claim 1 including an annular washer located intermediate the valve and disc.

3. The assembly of claim 2 wherein the washer has an outward taper.

4. The assembly of claim 1 wherein the body member has an annular shoulder adjacent a distal end of the cavity, and in which the valve is engaged against the shoulder.

5. The assembly of claim 1 wherein the body member includes an annular flange located intermediate the disc and sleeve.

6. A valve assembly adapted for receiving an elongated element such as a catheter, comprising:

a hollow body member having a cavity;

a compression member received on one end of the body member and having an annular flange aligned with the cavity;

a first elastic disc received in the cavity and having an opening extending therethrough;

a second elastic disc received in the cavity and having an opening extending therethrough;

a cylindrical elastic sleeve received in the cavity, located intermediate the first and second discs, and having an axial bore circumferentially surrounded by an annular wall, the radial thickness dimension for the annular wall being less than the axial length dimension of the sleeve;

said openings in said discs and sleeve bore being adapted to receive said elongated element and to seal against the outer surface of said element; and coupling means responsive to relative approach movement of the hollow body and compression member relative to the body member into a plurality of axially spaced apart positions for exerting different axial forces on the sleeve for inwardly bulging the sleeve, and for compressing the sleeve against the element by the relative approach movement of the annular flange toward the cavity, so that the sleeve permits passage of the element axially through the bore of the sleeve in a sleeve open position, immobilizes and holds the element in the bore of the sleeve in a sleeve gripping position, and after removal of the element from the bore of the sleeve, prevents flow of fluid, such as air or blood, through the bore of the sleeve in a sleeve bulged inwardly position.

7. The valve assembly of claim 6 wherein the coupling means comprises cooperating threads on the body member and compression member.

8. The assembly of claim 6 wherein the opening of at least one of said discs comprises a plurality of slits.

9. The assembly of claim 6 wherein the external diameter of the sleeve is approximately equal to the outer edge of the first and second discs.

10. The assembly of claim 6 wherein the first disc is located farther into the cavity than the second disc.

11. A valve assembly for receiving an elongated element, such as a catheter, comprising:

a hollow member having a cavity;

a compression member received on one end of the body member and having an annular flange aligned with the cavity;

a first elastic disc having an opening extending therethrough and received in a distal portion of the cavity;

a separate second elastic disc having an opening extending therethrough and received in the cavity intermediate the first disc and the annular flange of the compression member;

a cylindrical elastic sleeve received in the cavity intermediate the second disc and the annular flange, and having a bore circumferentially surrounded by inner and outer surfaces of the sleeve, the sleeve thickness dimension between the inner and outer surfaces of the sleeve being less than the length dimension of the sleeve;

said openings in said discs and said sleeve bore being adapted to receive said elongated element and to seal against the outer surface of said element; and means for adjusting the compression member relative to the body member into a plurality of axially spaced apart positions for exerting different axial forces on the sleeve for inwardly bulging the sleeve, so that the sleeve permits passage of the element axially through the bore of the sleeve in a sleeve open position, immobilizes and holds the element in the bore of the sleeve in a sleeve gripping position, and after removal of the element from the bore of the sleeve, inhibits flow of fluid, including air and blood, through the bore of the sleeve in a sleeve bulged inwardly position.

12. The assembly of claim 11 wherein the opening of at least one of the discs comprises a plurality of slits.

13. The assembly of claim 11 wherein the body member has an annular shoulder adjacent the distal portion of the cavity, and in which the first disc is engaged against the shoulder.

14. The assembly of claim 13 wherein the shoulder has an outward tape, and in which the first disc has an outer wedge received in the shoulder taper.

15. The assembly of claim 11 including an annular washer intermediate the first and second discs.

16. The assembly of claim 15 wherein the washer has an outer inwardly directed taper, and in which the first and second discs have an outer wedge received in the taper of the washer.

17. The assembly of claim 15 including a second annular washer intermediate the second disc and sleeve.

18. The assembly of claim 17 wherein the second washer includes an outer inwardly directed taper and in which the second disc has an outer wedge received in the taper of the second washer.

19. The assembly of claim 17 wherein the body member has an annular shoulder in the cavity, and in which the second washer is fixedly secured by said shoulder.

20. The assembly of claim 17 wherein the body member has an internal thread, and in which the second washer has external threads to engage the body member threads.

21. The assembly of claim 11 where in the body member defines an annular shoulder to receive one of the discs.

22. The assembly of claim 21 wherein the shoulder has an outward taper, and in which the disc has an outer wedge received in the tapered portion of the shoulder.

23. The assembly of claim 11 wherein the body member has an annular shoulder intermediate the second disc and the sleeve.

24. The assembly of claim 23 wherein the shoulder has an outward taper adjacent the second disc, and in which the second disc has an outer wedge received in the taper.

* * * * *